(12) United States Patent
New et al.

(10) Patent No.: US 7,413,538 B1
(45) Date of Patent: Aug. 19, 2008

(54) EPITOPES FORMED BY NON-COVALENT ASSOCIATION OF CONJUGATES

(75) Inventors: Roger New, London (GB); Istvan Toth, Moggill (AU)

(73) Assignee: Mozaic Discovery Limited, Road Town, Tortola (VG)

( * ) Notice: Subject to any disclaimer, the term of this patent is extended or adjusted under 35 U.S.C. 154(b) by 766 days.

(21) Appl. No.: 10/019,052

(22) PCT Filed: Jun. 27, 2000

(86) PCT No.: PCT/GB00/02465

§ 371 (c)(1),
(2), (4) Date: Apr. 22, 2002

(87) PCT Pub. No.: WO01/01140

PCT Pub. Date: Jan. 4, 2001

(30) Foreign Application Priority Data

Jun. 28, 1999 (GB) .................................. 9915074.0

(51) Int. Cl.
C40B 40/00 (2006.01)
C40B 40/04 (2006.01)
C40B 40/10 (2006.01)
G01N 33/53 (2006.01)

(52) U.S. Cl. ............................ 506/18; 435/7.1; 506/13; 506/15

(58) Field of Classification Search .................. 506/18, 506/13, 15; 435/7.1
See application file for complete search history.

(56) References Cited

U.S. PATENT DOCUMENTS

| 5,580,563 A | 12/1996 | Tam |
| 5,851,536 A * | 12/1998 | Yager et al. .................. 424/400 |
| 5,882,645 A | 3/1999 | Toth et al. |
| 6,024,964 A | 2/2000 | Jung et al. |
| 6,074,650 A | 6/2000 | Jung et al. |
| 6,217,886 B1 * | 4/2001 | Onyuksel et al. ............. 424/401 |
| 2003/0095962 A1 * | 5/2003 | Ueda et al. ............... 424/130.1 |

FOREIGN PATENT DOCUMENTS

| WO | WO 95/02684 A1 * | 1/1995 |
| WO | WO 96/23881 A1 * | 8/1996 |

* cited by examiner

Primary Examiner—Mark L. Shibuya
(74) Attorney, Agent, or Firm—Rothwell, Figg, Ernst & Manbeck P.C.

(57) ABSTRACT

A composition for interacting with a ligand, which composition comprises a non-covalent association of a plurality of distinct conjugates, each conjugate comprising a head group and a tail group, wherein the tail groups of the conjugates form a hydrophobic aggregation and the conjugates are movable within the association so that, in the presence of a ligand, at least two of the head groups are appropriately positioned to form an epitope capable of interacting with the ligand more strongly than each of head groups individually.

12 Claims, 2 Drawing Sheets

EPITOPES FORMED BY NON-COVALENT ASSOCIATION OF CONJUGATES

The present invention relates to a composition for interacting with a ligand, a method for producing such a composition and a method for producing a molecule based on the composition.

BACKGROUND OF THE INVENTION

Protein receptors are known normally to bind to their target ligands via epitopes, which constitute a small proportion of the total protein molecule. For maximum binding or interaction, the structure of the epitope needs to be maintained in a rigid conformation in order to form a binding site containing all the necessary components of the epitope in close proximity. Attempts to produce an analogous peptide constructed solely of the amino acids comprising the binding site often fail because these peptides do not possess the same biological activity as the protein receptor. This is attributed to the peptide having a different conformation in free solution from that of the entire protein receptor. In addition, where the binding site of a protein is constructed of oligo-peptides from different, non-contiguous parts of a protein chain, mixing isolated oligopeptides in free solution does not result in reconstitution of the active binding site.

Being constrained to use such large proteins to present binding-site epitopes gives rise to several problems in development of new receptor-specific therapeutic strategies. One problem is that such large proteins can readily evoke an immune response. A second problem is that long peptide chains are susceptible to attack by endopeptidases, such as those in the lumen of the gut. Finally, these large proteins can be costly to manufacture, purify and maintain in stable form.

SUMMARY OF THE INVENTION

The present invention aims to overcome the disadvantages of the prior art.

In a first aspect, the invention provides a composition for interacting with a ligand, which composition comprises a non-covalent assembly of a plurality of distinct conjugates, each conjugate comprising a head group and a tail group, wherein the tail groups of the conjugates form a hydrophobic aggregation and the conjugates have freedom of motion with respect to each other within the assembly so that, in the presence of a ligand, at least two of the head groups (which are the same or different) are appropriately positioned to form an epitope capable of interacting with the ligand more strongly than each of head groups individually. The head groups are typically hydrophilic and the tail groups typically hydrophobic, eg lipophilic, composed of hydrocarbon chains, halophilic, constructed of fluorocarbon chains, or silane based.

By constructing conjugates with a head group and a tail group in accordance with the present invention, the tail groups can associate to form a hydrophobic aggregation which is typically a supramolecular assembly such as a micelle, a lamellar structure, a liposome or other lipid structure, in which the conjugate are oriented whereby the head groups are brought into close proximity when in an aqueous phase. Because the conjugates are movable within the assembly, the head groups are able to adopt a number of different positions within the assembly. The head groups, which are typically non-identical, are therefore free to move within the assembly and, surprisingly, to interact cooperatively to induce biological consequences which the head groups on their own are not capable of eliciting. A further unexpected finding is that assemblies composed of combinations of different headgroups are capable of eliciting biological responses or participating in binding with biological receptors while assemblies composed of single headgroups are not capable of acting in this way.

As indicated above, these supra-molecular assemblies are typically particulate or colloidal in nature, usually comprising many hundreds of sub-units (the conjugates) all oriented with the headgroups directed outwards from the centre of the particle as shown in FIG. 1a. Each of the conjugates may change its location within the assembly, being free to exchange places with adjacent conjugates by a process of Brownian motion and, in so doing, may migrate over the whole surface of the assembly. Other manifestations of supra-molecular assemblies are cubic phases and coated surfaces.

Each conjugate in the assembly may have a head group selected from one chemical or biological class or a number of different classes, such as an amino acid or peptide; a peptide analogue; a mono-, di- or poly-saccharide; a mono-, di- or poly-nucleotide; a sterol; an alkaloid; an isoprenoid; an inositol derivative; a single or fused aromatic nucleus; a water-soluble vitamin; a porphyrin or haem nucleus; a phthalocyanine; a metal ion chelate; a water-soluble drug; a hormone; or an enzyme substrate.

In one preferred embodiment, each head group comprises an amino acid or oligo-peptide, which may be the terminal portion of a peptide chain. It is desirable to keep the length of the peptide to a minimum so as to avoid eliciting an immune response where the composition is to be used in vivo. Accordingly, it is preferred that the peptide is no more than six amino acids long.

The amino acids employed can be any of the natural amino acids, substituted derivatives, analogues, and D-forms thereof.

The tail groups of the conjugates may be all the same or may be a mixture of different tail groups, each of which preferably comprises a hydrophobic group selected from a linear, branched, cyclic, polycyclic, saturated or unsaturated construct, with or without hetero-atoms included in the structure which can be substituted or unsubstituted, for example, a lipidic amino acid analogue; a prostaglandin; a leukotriene; a mono- or diglyceride; a sterol; a sphingosine or ceramide derivative; and a silicon or halogen-substituted derivative of such a hydrophobic group. The tail group preferably has from 6 to 24 carbon atoms and more preferably comprises from 10 to 14 carbon atoms. More than one tail group may be present in each conjugate. For example, one or more lipidic amino acids with hydrocarbon side chains may form part of each conjugate, linked to one or more amino acids in the head group.

Any chemical method may be used to link the head group to the tail group. For example, each conjugate may further comprise a spacer group linking the head group to the tail group so as to facilitate presentation of the head group on the surface of the non-covalent association. Such spacer groups are well known and include, for example, amino acids, hydroxy acids, sugars and polyethylene glycol.

In a further aspect, the present invention provides a composition as defined above, for use as a medicament, a prophylactic or a diagnostic.

An advantage of the invention is that strong specific binding interactions can be achieved with conjugates in which the head groups are small in comparison to conventional biological receptors. If the head group is an oligo-peptide, for example, then the length of the peptide chain would not normally exceed ten amino acids and would preferably be six or less. Accordingly, compositions according to the present invention can be made far less immunogenic than their protein counterparts.

In accordance with this aspect of the invention, not only can the composition of the present invention be formulated to interact with a ligand in vitro but also the composition can be used in vivo, optionally formulated with a suitable diluent, excipient or carrier in accordance with a suitable delivery route.

In a further aspect, the present invention provides use of a conjugate comprising a head group and tail group for the preparation of the composition as defined above.

There is further provided a method for producing a composition for interacting with a ligand, which method comprises:

(a) providing a plurality of distinct conjugates, each conjugate comprising a head group and a tail group; and (b) forming from the plurality of conjugates, by noncovalent association thereof, an assembly in which the tail groups aggregate hydrophobically and in which the conjugates exhibit freedom of motion relative to one another so that, in the presence of a ligand, at least two of the head groups are appropriately positioned to form an epitope capable of interacting with the ligand more strongly than each of head groups individually. Each conjugate is preferably as defined above.

The conjugates may be dispersed in aqueous phase by a variety of known methodologies for the preparation of lipid vesicles, including mechanical mixing, exposure to high shear forces, sonication, solvent dispersion or codissolution with detergents. Typically, the non-covalent supra-molecular assemblies formed thereby will be composed of several different conjugates mixed together. Additional lipidic materials may optionally be added to alter surface properties, to aid in the dispersion of the conjugates, to stabilise the non-covalently associated assembly of conjugates, to aid in the presentation of head groups of the conjugates, or to permit the construction of vehicles which can be targeted by the epitopes formed upon random movement of the conjugates and appropriate positioning of the head groups within the assembly.

An important aspect of the method according to the present invention involves the step of identifying the plurality of conjugates which has the desired biological activity. In a preferred aspect, this step comprises (i) selecting a set of conjugates with an array of head groups;

(ii) forming a non-covalent association therefrom, in which the tail groups aggregate hydrophobically and in which the conjugates exhibit freedom of motion with respect to one another;

(iii) assaying for sufficient interaction between the non-covalent association and the ligand;

(iv) optionally repeating steps (i) to (iii) using a set of conjugates with a modified array of head groups; and (v) on finding sufficient interaction in step (iii), selecting the set of conjugates as the plurality of conjugates in step (a).

Examples of assays for "sufficient interaction" may include binding assays such as those utilising the ELISA principle for detection of association between antibody and antigen. Other suitable in vitro assays include modification of fluorescence of environmentally-sensitive membrane-bound fluorescent probes, precipitation reactions, enhancement or inhibition of enzyme activity etc. Assays relying on the ability of materials to alter the behaviour of cells cultured in vitro may also be appropriate, such as assays for cell death, cell proliferation, apoptosis, inhibition or stimulation of cell-to-cell contact, secretion of cytokines or other soluble products, synthesis of specific m-RNA, intracellular vesicular transport, alteration of cell signalling processes etc. In vivo assays in whole animals or humans may also be carried out, for example incorporation of radiolabel into the supramolecular assemblies, followed by investigation of its subsequent distribution after administration by various routes.

According to this method a combinatorial approach is used in which a range of different supra-molecular assemblies (or "probes") is prepared, each containing a different combination of conjugates selected from a pre-synthesised bank. Selection of the appropriate conjugates may be based on known properties of the target ligand or may simply involve the use of a very wide range of head groups to increase the probability that two or more of the head groups will form an epitope for the ligand. In this way, following the assay for sufficient interaction between the probe and the ligand as described above, the combination of conjugates found to be most effective may be modified by adding further head groups, removing some head groups, or both, and assaying the resultant probes once again for sufficient interaction. Eventually, the most favourable combination of head groups may be identified and selected for use in the composition.

The present invention therefore has a very clear advantage over traditional combinatorial chemistry. In combinatorial chemistry, the identification of the most favourable sequence for binding to a specific receptor must be carried out by synthesis of hundreds of possible combinations of different groups such as amino acids, in different orders, each one having to be tested for efficacy. This process is time-consuming, expensive and is limited by the nature of the chemistry which can be carried out in linking the different components together. In contrast, the present invention simply relies upon proximity of the head groups to provide association-derived epitopes. Once a set of conjugates has been synthesised, no further synthetic chemistry is required, only simple mixing of the conjugates to form the different probes by non-covalent association.

In a preferred simple embodiment, the present method uses conjugates having a single terminal amino acid linked via a spacer to a lipid tail group which can be combined simply by mixing in aqueous medium to form micelles in which different amino acid side chains would be presented together in a multiplicity of different configurations. Accordingly, the need to present amino acids in a specific order, or with a specific spacing or orientation, is circumvented. On statistical grounds, a proportion of the individual amino acid sub-units will always be associated in an ideal configuration.

In one arrangement, each of the conjugates would have the linear structure: X-spacer-spacer-lipid-lipid, where X represents a single amino acid different for each of the distinct conjugates employed.

When seeking to construct epitopes composed of natural amino acids it is possible to simplify further the number of head groups for selection. One can categorise the amino acid residues found in natural proteinaceous materials into six fundamental classes preferably using in any one class one amino acid rather than all members of that class because of the increased spatial flexibility of amino acids in the terminal position of the head group. This has the effect of reducing considerably the total number of amino acids required for constructing the pre-synthesised bank of conjugates and thereby the total number of head groups used. The main classes of amino acids are set out in Table 1 below.

TABLE 1

| Class | Representative | Abbreviation |
|---|---|---|
| Hydrophobic | Leucine | L |
| Hydroxylic | Serine | S |
| Acidic | Glutamate | E |
| Amide | Glutamine | Q |
| Basic | Histidine | H |
| Aromatic | Tyrosine | Y |

A number of strategies are available for identifying active combinations of amino acid-containing conjugates.

In one embodiment, a restricted number of conjugates is employed to form a range of distinct probes where each probe is an aqueous suspension of supra-molecular assemblies, each assembly consisting of selected conjugates mixed together, and each differing from the other as a result of the inclusion of a different additional conjugate as shown below where each of the letters given represents a conjugate with a different terminal amino acid:

| Probe 1 | A | B | C | D |
|---|---|---|---|---|
| Probe 2 | A | B | C | E |
| Probe 3 | A | B | C | F |
| Probe 3 | A | B | C | G |
| ... | | | | |
| ... | | | | |
| Probe x | A | B | C | Z |

Each of the probes is tested separately in the biological assays for sufficient binding as outlined above.

In a second simple embodiment, an initial probe can be constructed which contains a large number of different conjugates from the bank, and its efficacy compared with probes each lacking a different conjugate in turn, to determine which headgroups in the bank are essential, and which are redundant for the biological interaction being investigated. This approach is illustrated below:

| Probe 1 | A | B | C | D E . . . Z |
|---|---|---|---|---|
| Probe 2 | A | C | D | E . . . Z |
| Probe 3 | A | B | D | E . . . Z |
| ... | | | | |
| Probe x | A | B | C | D E . . . |

Combinations of the alternative approaches as outlined above can be made.

A knowledge of the target ligand may assist in designing a suitable starting array. For example, if the ligand is known to be basic, it would make sense to impart an acidic character to the conjugates by presenting them in the form where a free carboxyl group of the terminal amino acid is exposed. Introducing additional functionality by employing a particular amino acid as a spacer group adjacent to the terminal amino acid may also confer increased specificity. Where the involvement of, say. a short oligo-peptide sequence of known structure has already been implicated in binding to the target ligand, such a sequence may be incorporated into a conjugate to be included in the set of conjugates making up the composition.

In a final aspect, the present invention provides a method for producing a molecule for interacting with a ligand. The method comprises producing a composition according to one of the methods defined above; identifying the at least two head groups which form an epitope for the ligand in the composition; and producing a molecule incorporating the functional groups of the at least two head groups optionally spaced apart by one or more linker groups so that the molecule is capable of interacting with the ligand more strongly than each of the head groups individually.

Whilst the compositions of the present invention may themselves be useful in in vitro or in vivo systems perhaps to induce a biological response in a therapeutic, prophylactic or diagnostic method, in some circumstances a molecule may be produced based on the structure of the above compositions. By identifying the functional groups of the at least two head groups which form the epitope for the ligand a new molecule analogous to the composition may be produced containing the same or a similar epitope. The functional groups may, for example, be incorporated into a single linear oligo-peptide possibly with one or more linker groups to space the functional groups apart.

BRIEF DESCRIPTION OF THE DRAWINGS

The invention will now be described in further detail, by way of example only, with reference to the following Examples and the attached drawings, in which.

DETAILED DESCRIPTION OF THE INVENTION

Figure 1:
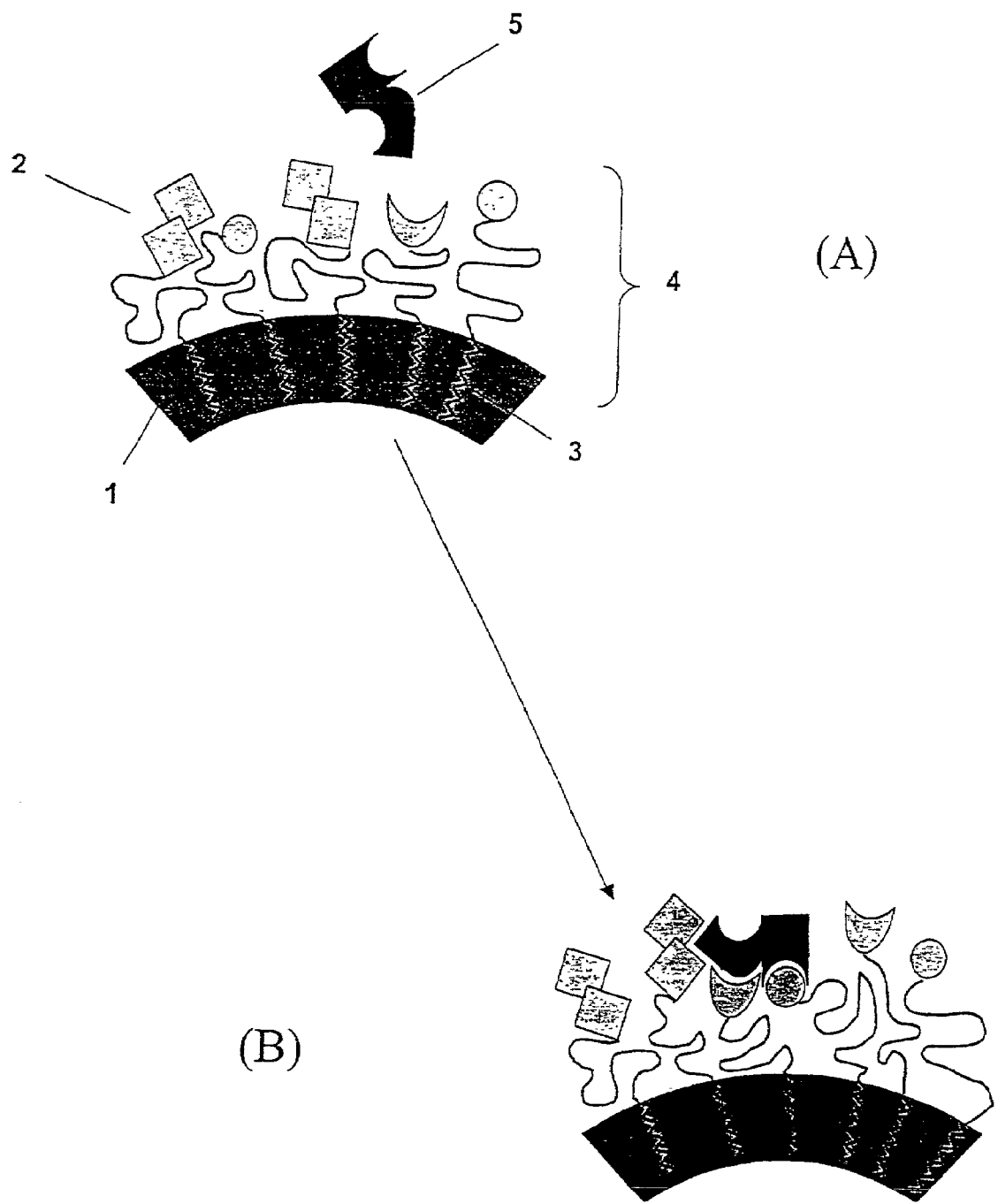
FIG. 1 shows a schematic representation of the surface of a supra-molecular assembly, and how such a composition according to the present invention binds to a target ligand.
Figure 2:
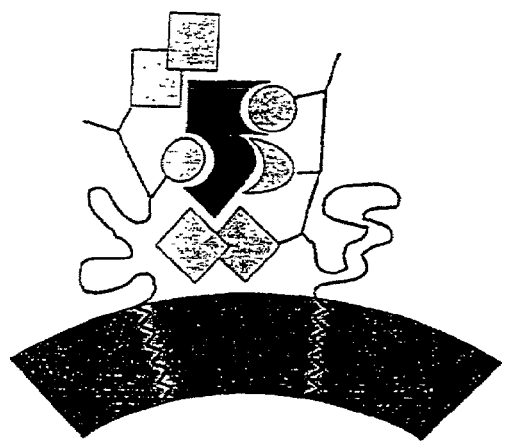
FIG. 2 shows a schematic representation of the surface of a supra-molecular assembly composed of two non-identical conjugates whose headgroups consist of short-chain linear peptides.
Figure 2:
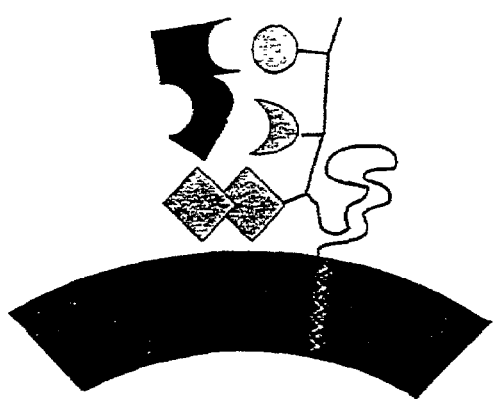
Figure 2:
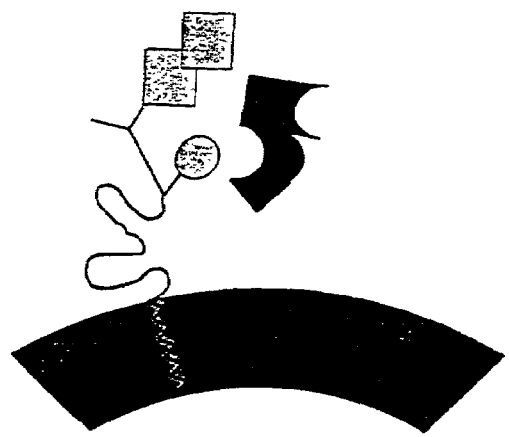

Referring to FIG. 1, a section 1 of a composition according to the present invention is shown in the form of a micelle in which the head groups 2 and tail groups 3 together form conjugates 4 (FIG. 1A). A target ligand 5 is presented to the composition 1. Because the conjugates are movable, a rearrangement occurs (FIG. 1B) to allow positioning of the head groups 2 to bind the target ligand 5. Referring to FIG. 2, a section of a composition according to the present invention is shown in the form of a supramolecular assembly, in which binding of a ligand to the surface of the assembly is brought about by the creation of an epitope constructed via the non-covalent association of two conjugates composed of short-chain peptides (A), this epitope being able to interact with the ligand more strongly than either of the individual conjugates in isolation (B). The same principle applies for headgroups containing structures other than amino acids.

EXAMPLES

In the examples given below, the standard convention for representation of amino acids by single letters of the alphabet is employed, except that in all cases the letter refers to conjugates as described above in which that particular amino acid occupies the terminal position in the peptide chain. In the examples described here, the lipid comprises two amino acids linked via a peptide bond, in which both of the amino acids are glycine analogues, where in each case the alpha hydrogen has been replaced by a linear hydrocarbon chain containing either 12 or 14 carbons. Linkages between the headgroup and spacer and the spacer and lipid are all via peptide bonds. The headgroup bears a free amino group and the free end of the lipid bears a $CONH_2$ group. The structure of each conjugate is thus: $NH_2$-headgroup-spacer-amino acid ($C_{14}$ side chain)-amino acid ($C_{12}$ side chain)-$CONH_2$.

Example 1

Stimulation of TNF Secretion from Macrophages

1. Individual conjugates E, Y, Q, S & H (linked to lipid via a serine-glycine spacer) were prepared as solutions in methanol/dichloromethane 1:1 at a concentration of 5 mg/ml.
2. Solutions of the conjugates were dispensed into 7 ml glass vials in equal proportions, to give a final volume of 400 ul (2 mg of solid) in all vials, as shown in the example overleaf. In cases where the volume of organic solution available was insufficient, adjustment was made at a later stage, when the quantity of water added for reconstitution was reduced accordingly, as shown.
3. The contents of all vials were dried down under a stream of nitrogen, then exposed to a vacuum of at least 1 mbar overnight in a lyophiliser.
4. On the following day, distilled water was added in volumes as indicated in the table overleaf, to give a final concentration in all vials of 1 mg/ml. The vials were capped, warmed to 37 deg C. and bath-sonicated until clarity was achieved.
5. The samples were then applied to wells of 24-well cluster plates into which cells of the J774A-1 macrophage cell line had been plated ($5 \times 10^4$ cells/ml/well). Volumes of 100 ul and 10 ul of sample were added to individual wells, and the cells were incubated overnight at 37 deg C. in an atmosphere of 5% $CO_2$/air.
6. The following day, duplicate volumes of 50 ul of supernate were taken from each well and measured for TNF concentration in a capture ELISA assay. Results obtained are shown in the table below.

|  | Volume of conjugate dispensed | | | | | Volume of water added |
| --- | --- | --- | --- | --- | --- | --- |
|  | E | Y | Q | S | H |  |
| E | 260 ul | | | | | 1.3 ml |
| Y | | 400 ul | | | | 2.0 ml |
| Q | | | 310 ul | | | 1.55 ml |
| S | | | | 360 ul | | 1.8 ml |
| H | | | | | 400 | 2.0 ml |
| EY | 200 ul | 200 ul | | | | 2.0 ml |
| EQ | 200 ul | | 200 ul | | | 2.0 ml |
| ES | 200 ul | | | 200 ul | | 2.0 ml |
| EH | 200 ul | | | | 200 ul | 2.0 ml |
| YQ | | 200 ul | 200 ul | | | 2.0 ml |
| YS | | 200 ul | | 200 ul | | 2.0 ml |
| YH | | 200 ul | | | 200 ul | 2.0 ml |
| QS | | | 200 ul | 200 ul | | 2.0 ml |
| QH | | | 200 ul | | 200 ul | 2.0 ml |
| SH | | | | 200 ul | 200 ul | 2.0 ml |
| QSH | | | 133 ul | 133 ul | 133 ul | 2.0 ml |
| YSH | | 133 ul | | 133 ul | 133 ul | 2.0 ml |
| YQH | | 133 ul | 133 ul | | 133 ul | 2.0 ml |
| YQS | | 133 ul | 133 ul | 133 ul | | 2.0 ml |
| ESH | 133 ul | | | 133 ul | 133 ul | 2.0 ml |
| EQH | 133 ul | | 133 ul | | 133 ul | 2.0 ml |
| EYH | 133 ul | 133 ul | | | 133 ul | 2.0 ml |
| EYS | 133 ul | 133 ul | | 133 ul | | 2.0 ml |
| EYQ | 133 ul | 133 ul | 133 ul | | | 2.0 ml |
| EQS | 133 ul | | 133 ul | 133 ul | | 2.0 ml |
| EYQS | 50 ul | 50 ul | 50 ul | 50 ul | | 1.0 ml |
| EYQH | 50 ul | 50 ul | 50 ul | | 50 ul | 1.0 ml |
| EYSH | 50 ul | 50 ul | | 50 ul | 50 ul | 1.0 ml |
| EQSH | 50 ul | | 50 ul | 50 ul | 50 ul | 1.0 ml |
| YQSH | | 50 ul | 50 ul | 50 ul | 50 ul | 1.0 ml |
| EYQSH | 40 ul | 40 ul | 40 ul | 40 ul | 40 ul | 1.0 ml |

| | $OD_{450}$ in J774 supernates | | |
| --- | --- | --- | --- |
| | 100 ug | 10 ug | 0 ug |
| E | 0.628 | 0.098 | 0.013 |
| Y | 0.313 | 0.053 | |
| Q | 0.083 | 0.015 | |
| S | 0.348 | 0.143 | |
| H | 0.632 | 0.206 | |
| EY | 0.198 | 0.027 | |
| EQ | 0.113 | 0.022 | |
| ES | 0.211 | 0.225 | |
| EH | 0.167 | 0.037 | |
| YQ | 0.245 | 0.034 | |
| YS | 0.786 | 0.363 | |
| YH | 0.541 | 0.133 | |
| QS | 0.212 | 0.025 | |
| QH | 0.135 | 0.027 | |
| SH | 0.515 | 0.177 | |
| QSH | 0.253 | 0.032 | |
| YSH | 0.712 | 0.229 | |
| YQH | 0.290 | 0.020 | |
| YQS | 0.519 | 0.119 | |
| ESH | 0.380 | 0.246 | |
| EQH | 0.107 | 0.026 | |
| EYH | 0.254 | 0.042 | |
| EYS | 1.289 | 0.355 | |
| EYQ | 0.191 | 0.064 | |
| EQS | 0.209 | 0.027 | |
| EYQS | 0.777 | 0.206 | |
| EYQH | 0.224 | 0.067 | |
| EYSH | 0.262 | 0.146 | |
| EQSH | 0.149 | 0.185 | |
| YQSH | 0.319 | 0.045 | |
| EYQSH | 0.375 | 0.073 | |

It can be seen that some, but not all, of the combinations of different headgroups elicit strong biological responses, indicating that the response is specific to those particular combinations. The example illustrates the way in which the conjugates described can be employed in the combinatorial approach to identify efficacious combinations for the purpose of eliciting a desired biological response.

Example 2

TNF Secretion from Macrophages

Comparison of Supra-Molecular Assemblies Containing a Mixture of Conjugates, with a Mixture of Supra-Molecular Assemblies Each Containing a Single Conjugate Samples were prepared as described in Example 1, with or without the inclusion of additional lipidic materials as described below. The combination of conjugates Y, S and L was chosen since this combination was a good performer in the experiment described in Example 1.

Probes containing phosphatidyl choline were prepared at a ratio of phospholipid to conjugate of 2:1 wt/wt.

Probes containing octyl glucoside were prepared at a ratio of glycolipid to conjugate of 1:1 wt/wt.

Results shown in the table below are optical densities at 450 nm of TNF ELISAs conducted on 18 hour culture supernatants. The concentration of conjugate in the wells was 10 ug/ml.

|  | OD$_{450}$ of TNF ELISA |
|---|---|
| EYS | 0.390 |
| E + Y + S | 0.059 |
| medium control | 0.000 |
| EYS:OG | 0.559 |
| (E + Y + S):OG | 0.193 |
| OG control | 0.228 |
| EYS:PC | 0.320 |
| (E + Y + S):PC | 0.130 |
| PC control | 0.031 |

This example shows that combinations of the conjugates can elicit biological responses either when presented alone, or when presented in conjunction with other lipids, such as phospholipids or lipid sugars. It also shows that for efficacy to be manifested, it is important for all of the conjugates to be presented in combination on the same supra-molecular assembly, and that activity is not observed if the same conjugates are presented together at the same time, but separated on different supra-molecular assemblies. This suggests that it is important to present the conjugates in close proximity to each other, in order to permit the formation of epitopes formed by non-covalent association of the conjugates, which can participate in specific binding with cell-surface receptors.

Example 3

Enhancement of Oral Uptake

1. Individual conjugates L, S, E & Q (conjugated to lipid via a tyrosine-glycine spacer) were prepared as solutions in benzyl alcohol at a concentration of 10 mg/ml.
2. 75 ul of $^{14}$C-cholesterol oleate (3.7 MBq/ml in toluene) was dispensed into four 7 ml glass screw-capped vials and dried down under a stream of nitrogen.
3. 400 ul of each of the solutions in (1) was added to one of the vials in (2) and shaken overnight at room temperature.
4. Solutions of the conjugates were dispensed into 7 ml glass vials in equal proportions, to give a final volume of 80 ul (0.8 mg of solid) in all vials, as shown in the example below.

|  | L | S | E | Q |
|---|---|---|---|---|
| L | 80 ul | — | — | — |
| S | — | 80 ul | — | — |
| E | — | — | 80 ul | — |
| Q | — | — | — | 80 ul |
| LS | 40 ul | 40 ul | — | — |
| LE | 40 ul | — | 40 ul | — |
| LQ | 40 ul | — | — | 40 ul |
| SE | — | 40 ul | 40 ul | — |
| SQ | — | 40 ul | — | 40 ul |
| EQ | — | — | 40 ul | 40 ul |
| LSE | 27 ul | 27 ul | 27 ul | — |
| LSQ | 27 ul | 27 ul | — | 27 ul |
| LEQ | 27 ul | — | 27 ul | 27 ul |
| SEQ | — | 27 ul | 27 ul | 27 ul |
| LSEQ | 20 ul | 20 ul | 20 ul | 20 ul |

5. 2 ml of distilled water was added to each of the vials with vortexing. The vials were then capped and bath-sonicated for 20 minutes.
6. The samples were then frozen in liquid nitrogen and lyophilised overnight.
7. The following day, each vial was reconstituted with 2 ml of distilled water and sonicated again until clear dispersions were achieved.
8. The samples were administered by oral gavage to Balb/c female mice (20-25 g weight—four mice per group) at a dose of 0.3 ml per animal.
9. 75 ul heparinised blood samples were taken by tail venupuncture at 45, 90 and 180 minutes after administration.
10. Each sample was diluted in 0.5 ml of PBS, which was then centrifuged, and 0.4 ml of the supernate was transferred to a scintillation vial to which 2 ml of Optiphase Hisafe 3 (Wallac) was added with mixing.
11. Activity in the samples was measured in a scintillation counter.

Percentage uptake was estimated on the basis of a 2 ml blood volume, of which 1 ml was assumed to be plasma. Results are shown in the table below.

|  | % uptake in bloodstream | | |
|---|---|---|---|
|  | 45 mins | 90 mins | 180 mins |
| L | 0.90 | 1.39 | 0.61 |
| S | 1.12 | 1.14 | 0.81 |
| E | 0.85 | 1.55 | 0.79 |
| Q | 1.40 | 3.00 | 0.81 |
| LS | 2.87 | 2.38 | 0.66 |
| LE | 2.59 | 2.22 | 0.49 |
| LQ | 5.05 | 2.15 | 0.45 |
| SE | 4.21 | 1.66 | 0.70 |
| SQ | 4.67 | 1.45 | 0.67 |
| EQ | 3.72 | 2.65 | 0.59 |
| LSE | 1.91 | 1.20 | 0.97 |
| LSQ | 6.23 | 1.90 | 0.80 |
| LEQ | 2.77 | 1.73 | 0.98 |
| SEQ | 3.06 | 1.52 | 0.63 |
| LSEQ | 2.45 | 1.74 | 0.81 |

It can be seen that some, but not all, of the combinations of different headgroups enhance uptake of label via the oral route, indicating that the response is specific to those particular combinations. The example illustrates the way in which the conjugates described can be employed in the combinatorial approach to identify efficacious combinations capable of acting as targeting ligands.

Example 4

ELISA Fc Binding 1. 100 ul of goat IgG (1 mg/ml) was added to 20 ml of PBS and 100 ul was placed in each well of a flat-bottomed microtitre plate.
2. The plate was incubated for several days at +4 deg C.
3. 2 mg of each of the conjugates Y, F, W, L, S, E, Q & R (each linked to lipid via a serine-glycine spacer) were weighed into 1 ml glass vials and 200 ul of benzyl alcohol added to give solutions of each conjugate at a concentration of 10 mg/ml.
4. The solutions were dispensed in 7 ml glass screw-capped vials as follows:

| Vial No. | Y | F | W | L | S | E | Q | R |
|---|---|---|---|---|---|---|---|---|
| 1 | 20 ul | 20 ul | 20 ul | — |  |  |  |  |
| 2 | 20 ul | 20 ul | — | 20 ul |  |  |  |  |
| 3 | 20 ul | — | 20 ul | 20 ul |  |  |  |  |
| 4 | — | 20 ul | 20 ul | 20 ul |  |  |  |  |
| 5 |  |  |  |  | 20 ul | 20 ul | 20 ul | — |

-continued

| Vial No. | Y | F | W | L | S | E | Q | R |
|---|---|---|---|---|---|---|---|---|
| 6 | | | | | 20 ul | 20 ul | — | 20 ul |
| 7 | | | | | 20 ul | — | 20 ul | 20 ul |

5. The contents of each vial were mixed well by vortexing, then 1.5 ml of distilled water was added to each vial.
6. The vials were capped and bath-sonicated for five minutes to give crystal clear dispersions.
7. The plate from step (2) was washed in PBS/0.02% Tween 20 and then blocked by incubating for one hour with 1% BSA in PBS (300 ul/well).
8. The plate was then washed as before, and 100 ul of sample from each of the vials in step (6) was added to wells in column (1) of rows (1) to (7) Row (8) was left as a blank control.
9. Doubling dilutions were performed across the plate by transferring 100 ul from wells in column (1) to the adjacent well on the same row in column (2) and mixing, then transferring 100 ul to the next column as before, etc.
10. The plate was then incubated overnight at +4 deg C.
11. The following day, the plate was washed as before and 100 ul of commercial horseradish peroxidase-IgG conjugate (diluted 1/1000 in PBS) was added to each well and incubated at room temperature for 40 minutes.
12. The plate was then washed again, and 100 ul of OPD substrate for peroxidase was added to each well and incubated at room temperature for 30 minutes.
13. 20 ul of 3M sulphuric acid was then added to each well to stop the reaction.
14. The optical density of each of the wells was measured at 450 nm on a plate reader, and the results obtained, after adjustment for background, are recorded below.

| Sample | 1 in 4 | 1 in 8 | 1 in 16 | 1 in 32 | 1 in 64 |
|---|---|---|---|---|---|
| 1 YFW | 0.001 | 0.039 | 0.048 | 0.053 | 0.083 |
| 2 YFL | 1.504 | 1.484 | 1.325 | 0.723 | 0.051 |
| 3 YWL | 0.803 | 0.192 | 0.022 | 0.023 | 0.060 |
| 4 FWL | 1.034 | 0.778 | 0.208 | 0.031 | 0.034 |
| 5 SEQ | 0.029 | 0.041 | 0.055 | 0.057 | 0.091 |
| 6 SER | 0.013 | 0.030 | 0.044 | 0.062 | 0.075 |
| 7 SQR | 0.000 | 0.045 | 0.031 | 0.054 | 0.065 |

It can be seen that maximal binding is achieved with samples 2, 3 and 4 (ie combinations YFL, YWL, and FWL).

It can be seen that some, but not all, of the combinations of different headgroups enter into strong binding interactions, indicating that the response is specific to those particular combinations. The example illustrates the way in which the conjugates described can be employed in the combinatorial approach to identify efficacious combinations for the purpose of eliciting a desired binding interaction.

The invention claimed is:

1. Isolated micelles, comprising:
    a plurality of conjugate molecules non-covalently associating with one another to form the micelles, each conjugate molecule comprising
    a head group molecule conjugated to a hydrophobic tail group molecule, optionally via a spacer molecule,
    a surface formed by the head group molecules, which surface comprises a plurality of distinct non-covalent associations of the head group molecules, and
    a hydrophobic core formed by the hydrophobic tail group molecules,
    wherein
    the head group molecules in the non-covalent associations change configuration through the movement of the head group molecules on or along the surface, and the movement of the head group molecules is facilitated by the movement of the conjugate molecules in the micelle, and
    a distinct non-covalent association of the head group molecules forms an epitope, which has higher affinity to a ligand than each of the head groups of the conjugates individually does.

2. A micelle according to claim 1, wherein each conjugate has a head group selected from the group consisting of: an amino acid or peptide; a peptide analogue; a mono- or polysaccharide; a mono- or poly-nucleotide; a sterol, a water-soluble vitamin; a porphyrin or haem nucleus; a metal ion chelate; a water-soluble drug; a hormone; and an enzyme substrate.

3. A micelle according to claim 1, wherein each head group comprises an amino acid.

4. A micelle according to claim 1, wherein each head group comprises a peptide comprising the amino acid.

5. A micelle according to claim 1, wherein the head groups which form the epitope comprise terminal amino acids selected from at least two of the following:
    hydrophobic amino acids, hydroxylic amino acids, acidic amino acids, amide amino acids, basic amino acids, and aromatic amino acids.

6. A micelle according to claim 1, wherein each tail group is the same or different and comprises a lipophilic group selected from a straight or branched-chain fatty acid, alcohol or aldehyde having at least 8 carbon atoms; a lipidic amino acid analogue; a prostaglandin; a leukotriene; a mono- or di-glyceride; a sterol; a sphingosine or ceramide derivative; and a silicon or halogen-substituted derivative of such lipophilic group.

7. A micelle according to claim 6, wherein each lipophilic group comprises a $C_{10}$ to $C_{14}$ fatty acid.

8. A micelle according to claim 1, wherein each conjugate further comprises a spacer group linking the head group to the tail group.

9. A micelle according to claim 8, wherein the spacer group is hydrophilic.

10. A micelle according to claim 8, wherein the spacer group comprises an amino acid, a hydroxy acid, a sugar or a polyethylene glycol.

11. An isolated micelle of claim 1, wherein each head group is an oligopeptide not exceeding 10 amino acids.

12. Isolated micelles of claim 1, which consist essentially of said plurality of conjugate molecules and a carrier.

* * * * *